United States Patent [19]

Wakameda et al.

[11] Patent Number: 4,917,904

[45] Date of Patent: Apr. 17, 1990

[54] PROCESS FOR THE PRODUCTION OF TRANSGLUTAMINASE-CONTAINING FOOD HAVING IMPROVED TEXTURE

[75] Inventors: Atsushi Wakameda; Nobuaki Yatsuka; Yasuhiko Sasamoto, all of Tokyo, Japan

[73] Assignee: Taiyo Fishery Co., Ltd., Tokyo, Japan

[21] Appl. No.: 310,720

[22] PCT Filed: Jun. 30, 1988

[86] PCT No.: PCT/JP88/00657

§ 371 Date: Feb. 3, 1989

§ 102(e) Date: Feb. 3, 1989

[87] PCT Pub. No.: WO89/00011

PCT Pub. Date: Jan. 12, 1989

[30] Foreign Application Priority Data

Jul. 2, 1987 [JP] Japan .................. 62-166021

[51] Int. Cl.$^4$ ............... A23L 1/313; A23L 1/315; A23L 1/325

[52] U.S. Cl. ......................... 426/7; 426/56; 426/59; 426/74

[58] Field of Search ............... 426/7, 641, 643, 42, 426/644, 56, 52, 47, 46, 32, 59, 74

[56] References Cited

FOREIGN PATENT DOCUMENTS 58-149645 9/1983 Japan .
59-59151 4/1984 Japan .
59-210097 11/1984 Japan .

Primary Examiner—Marianne Cintins
Attorney, Agent, or Firm—Frishauf, Holtz, Goodman & Woodward

[57] ABSTRACT

A process for the production of food having improved texture is disclosed wherein 0.001 to 5 parts by weight of transglutaminase is added to 100 parts by weight of a food material containing one or more materials selected from the group consisting of fish meat, animal meat and fowl.

13 Claims, No Drawings

PROCESS FOR THE PRODUCTION OF TRANSGLUTAMINASE-CONTAINING FOOD HAVING IMPROVED TEXTURE

TECHNICAL FIELD

This invention relates to a process for the production of food. More particularly, it relates to a process for the production of food having improved texture and properties or peculiar texture and properties which consists of adding transglutaminase to a food material containing fish meat, animal meat and, fowl, soybean protein, egg albumen or casein to thereby modify proteins contained therein.

BACKGROUND ART

Known methods for improving the texture and properties of food include physical ones such as heating, cooling, stirring or cutting a food material and chemical ones such as adding salt thereto or controlling the pH value thereof by adding an alkaline or acidic material thereto. Food mainly consists of proteins, lipids, saccharides, fibers, vitamins and inorganic matters and the texture, properties, color, taste, odor and nutritive value thereof can be varied by modifying these components. It is believed, in particular, that the texture and properties of food closely relate to proteins, lipids, saccharides and fibers contained therein. Thus it has been attempted to improve the properties of food by modifying these components.

Each of the known methods for improving the properties of food as described above exerts an intense physical or chemical effect on the components of food. Thus it would tend to damage, for example, the color, taste, odor or nutritive value of food. In addition, it restricts the process for the production or processing of food. Further these methods should be carried out under severe control, otherwise various troubles such as discoloration, an offensive taste, an offensive odor, the liberation of water or a decrease in the yield might occur.

Accordingly it is an object of the present invention to provide a process for the production of food whereby a food of improved texture and properties or peculiar texture and properties can be produced without being accompanied by any trouble as described above.

DISCLOSURE OF INVENTION

In order to achieve the above object, the present inventors have conducted extended studies. As a result, they have found that transglutaminase added to a food material containing specific proteins, such as fish meat, animal meat and fowl, soybean protein, egg albumen or casein, would exert a specific effect exclusively on the proteins contained in said food material and modify the same without affecting any component of the food material other than the proteins to thereby achieve the following improving effects (1) to (5) which are characteristic or in common depending on the proteins to be modified.

(1) When transglutaminase is added to a food material containing fish meat, the water retentivity of the food material is enhanced and the texture thereof becomes flexible and smooth.

(2) When transglutaminase is added to a food material containing animal meat and fowl, the water retentivity of the food material is enhanced and the texture thereof becomes hard to masticate.

(3) When transglutaminase is added to a food material containing soybean protein, the water retentivity of the food material is enhanced and the texture thereof becomes hard and smooth.

(4) When transglutaminase is added to a food material containing egg albumen, the foaming stability of the egg albumen is improved and the texture of the food material becomes smooth and soft.

(5) When transglutaminase is added to a food material containing casein, the viscosity of the food material is strengthened and the texture thereof becomes smooth.

The present invention, which has been completed based on this finding, provides a process for the production of food consisting of adding 0.001 to 5 parts by weight of transglutaminase to 100 parts by weight of a food material containing one or more materials selected from among fish meat, animal meat and fowl, soybean protein, egg albumen and casein.

Now the process for the production of food according to the present invention will be described in detail.

The food material to be modified by the transglutaminase in the present invention contains one or more materials selected from among fish meat, animal meat and fowl, soybean protein, egg albumen and casein. In the addition of the transglutaminase, the food material may be in any form depending on the type and the purpose of the use. Namely, the food material may be either mixed with other materials or not.

More particularly, examples of the food material containing fish meat include ground fish meat, minced fish meat, fillet and lyophilized fish meat powder. Examples of the food material containing animal meat and fowl include various minced animal meat and fowl and block meat. Examples of the food material containing soybean protein include soybean milk and soybean powder. Examples of the food material containing egg albumen include egg albumen as it is and processed egg such as dry egg albumen or frozen egg albumen. Examples of the food material containing casein include cow's milk, skim milk powder and casein powder.

Although it is preferable that the transglutaminase to be used in the present invention is a highly purified one, crude ones such as those obtained from bovine, equine or swine plasma or liver extract may be employed therefor.

The transglutaminase may be added in an amount of 0.001 to 5 parts by weight in terms of the pure enzyme, preferably 0.01 to b 5 parts by weight, to 100 parts by weight of the food material. When the amount of the transglutaminase is smaller than 0.001 part by weight, only a small amount of the transglutaminase would bind to the proteins in the food material, which results in only a limited effect. When it exceeds 5 parts by weight, on the other hand, the effect is achieved within a short period of time, which makes the processing of the food material difficult.

In the present invention, a calcium salt may be added together with the transglutaminase to the food material, if required, to thereby further enhance the improving effect. Examples of the calcium salt include calcium chloride, calcium carbonate, calcium sulfate and calcium phosphate.

It is preferable that the calcium salt is added in an amount of 0.001 to 2 parts by weight, still preferably 0.005 to 0.1 part by weight, to 100 parts by weight of the food material. When the amount of the calcium salt is smaller than 0.001 part by weight, only a limited effect is achieved. When it exceeds 2 parts by weight, on the other hand, it imparts an undesirable taste to the food. When the food material already contains 0.1 mM or more of calcium salt(s), the addition of any calcium salt is unnecessary.

In carrying out the present invention, thus, the above-mentioned transglutaminase may be added to the above-mentioned food material at a ratio within the range as defined above at any stage of the production or processing of the aimed food product. The food material containing the transglutaminase may be processed in a conventional manner depending on the purpose.

To further illustrate the present invention, the following Examples will be given.

EXAMPLE 1

3 g of common salt was added to 100 g of ground Alaska pollack meat and the resulting mixture was mixed with a small size high-speed cutter. Then 2 mg of a lyophilized transglutaminase powder was added thereto and the mixing was further continued. The paste thus obtained was filled in a vinyl tube and heated to 30° C. for one hour and to 90° C. for 20 minutes to thereby give a gel as the product of the present invention. For comparison, a control gel was produced in the same manner as the one described above except that no transglutaminase was added.

The properties of the product of the present invention obtained above and those of the control one were determined with a rheometer. Table 1 shows the jelly strength (JS), depression and whiteness of each product.

TABLE 1

|  | Product of invention | Control product |
| --- | --- | --- |
| JS (g) | 1260 | 1020 |
| Depression (mm) | 15.8 | 14.8 |
| Whiteness | 51.0 | 50.3 |

Table 1 suggests that the product of the invention is superior to the control one in all of the JS, depression and whiteness. As the result of an organoleptic test, the product of the invention was found to have a high water retentivity and a flexible texture, compared with the control one.

EXAMPLE 2

2 mg of a transglutaminase powder and 50 mg of calcium chloride were added to 100 g of egg albumen. The obtained mixture was whipped with a homogenizer and the foaming stability thereof was observed after 30 minutes. Table 2 shows the results.

TABLE 2

|  | Product of invention | Control product |
| --- | --- | --- |
| after 0 min | Fine and white foam | do |
| after 60 min | The foam hardly decreased and was still fine. | The foam decreased to ⅔. |

Table 2 suggests that the product of the invention containing transglutaminase is superior to the control one containing no transglutaminase in the foaming stability.

EXAMPLE 3

30 g of a lyophilized bovine plasma powder and 0.5 g of calcium chloride were added to 1000 ml of cow's milk. The resulting mixture was stirred and then heated to 30° C. for one hour. The milk thus obtained was processed in a conventional manner with the use of Bifidobacterium bifidus to thereby give a yogurt. As the result of an organoleptic test, this yogurt was found to be extremely smooth and highly viscous and have an excellent texture, compared with conventional ones.

EXAMPLE 4

1000 ml of soybean milk was slowly heated to approximately 70° C. and 7 g of calcium sulfate was added thereto under slow stirring. The obtained mixture was maintained at 70° C. for five minutes and then slowly cooled to a material temperature of 35° to 40° C. Then 10 mg of transgultaminase was added thereto and the resulting mixture was further slowly stirred. The proteinous suspension thus obtained was poured into a mold and solidified therein to thereby give a tofu-like food. The product thus obtained was hard and had a high water retentivity, compared with convnetional ones. It had a novel and smooth texture in the mouth and favorable.

EXAMPLE 5

30 g of egg albumen, 30 g of common salt, 30 g of bovine plasma protein and 1 g of calcium chloride were added to 1 kg of fine ground meat on shore SURIMI (2nd Grade) and thoroughly stirred. The resulting mixture was treated in a conventional manner to thereby give a heated gel as the product of the present invention. For comparison, a control product was produced in the same manner as the one described above except that no bovine plasma protein was added.

The properties of the product of the present invention obtained above and those of the control one were determined with a rheometer. Table 3 shows the JS, depression and whiteness of each product.

TABLE 3

|  | Product of invention | Control product |
| --- | --- | --- |
| JS (g) | 630 | 420 |
| Depression (mm) | 12.5 | 11.0 |
| Whiteness | 39.5 | 38.7 |

Table 3 suggests that the product of the present invention is superior to the control one in all of the JS, depression and whiteness.

EXAMPLE 6

30 g of bovine plasma protein and 1 g of calcium chloride were added to 100 g of egg albumen and the obtained mixture was foamed by homogenizing. Separately, 30 g of common salt and 500 g of water were added to 1 kg of fine ground meat on shore SURIMI (2nd Grade) and thoroughly stirred. Then the obtained mixture was mixed with the foamed egg albumen prepared above and molded. The molded product was heated to 90° C. for 20 minutes. The foamed ground fish meat gel thus obtained had an extremely smooth and soft texture.

EXAMPLE 7

700 g of salted minced lean pork, 300 g of lard, 250 g of water, 1 g of a phosphate, 1 g of calcium chloride and 30 g of a bovine plasma powder were mixed and stirred together. The obtained mixture was filled in a casing and smoked at 40° C. for 90 minutes and heated to 70° C. for 60 minutes to thereby give a sausage as the product of the present invention. For comparison, a control product was produced in the same manner as the one described above except no bovine plasma powder was added. The product of the present invention was superior to the control one in the resistance to the teeth and water retentivity, thus being favorable.

INDUSTRIAL APPLICABILITY

According to the process of the present invention, transglutaminase exerts a specific effect exclusively on proteins contained in food and thus modify the properties of the food without affecting any other component thereof. Thus the process of the present invention enables production of food of improved texture and properties or peculiar texture and properties without damaging, for example, the color, taste, odor or nutritive value of the food.

We claim:

1. A process for production of food having improved texture which consists of reacting 0.001 to 5 parts by weight of transglutaminase to 100 parts by weight of a food material containing one or more materials selected from the group consisting of fish meat, animal meat and fowl.

2. The process of claim 1 wherein 0.001 to 2 parts by weight of a calcium salt is further added to 100 parts by weight of said food material.

3. The process of claim 1 wherein said food material further contains egg albumen.

4. The process of claim 2 wherein said food material further contains egg albumen.

5. The process of claim 4 wherein said material is fish meat.

6. The process of claim 4 wherein said material is animal meat.

7. The process of claim 4 wherein said material is fowl.

8. The process of claim 2 wherein said material is fish meat.

9. The process of claim 2 wherein said material is animal meat.

10. The process of claim 2 wherein said material is fowl.

11. The process of claim 1 wherein said material is animal meat.

12. The process of claim 1 wherein said material is fish meat.

13. The process of claim 1 wherein said material is fowl.

* * * * *